(12) United States Patent
Heydorn et al.

(10) Patent No.: US 6,608,114 B1
(45) Date of Patent: Aug. 19, 2003

(54) PROCESS TO PRODUCE DME

(75) Inventors: Edward C. Heydorn, Macungie, PA (US); Bharat Lajjaram Bhatt, Fogelsville, PA (US); Barry W. Diamond, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/099,363

(22) Filed: Mar. 13, 2002

(51) Int. Cl.[7] ............................................... C07C 27/00
(52) U.S. Cl. ...................................... 518/707; 518/700
(58) Field of Search ................................. 518/700, 707

(56) References Cited

U.S. PATENT DOCUMENTS

| | | | |
|---|---|---|---|
| 4,031,123 A | 6/1977 | Espino et al. ............ | 260/449.5 |
| 5,218,003 A | 6/1993 | Lewnard et al. ............ | 518/700 |
| 5,750,799 A | 5/1998 | van Dijk ..................... | 568/698 |
| 6,147,125 A | * 11/2000 | Shikada et al. ............. | 518/713 |
| 6,191,175 B1 | * 2/2001 | Haugaard et al. ........... | 518/705 |

* cited by examiner

Primary Examiner—J. Parsa
(74) Attorney, Agent, or Firm—Robert J. Wolff

(57) ABSTRACT

A process is set forth for producing DME by dehydrating the effluent stream from a methanol reactor where the methanol reactor is a slurry bubble column reactor (SBCR) containing a methanol synthesis catalyst that converts a synthesis gas stream comprising hydrogen and carbon monoxide into an effluent stream comprising methanol. A key to the process is that the SBCR methanol can produce a relatively low water content methanol stream, thereby avoiding an intervening water removal unit between the SBCR methanol unit and the dehydration unit and/or an incremental increase in the water that must be processed by the dehydration unit.

6 Claims, 2 Drawing Sheets

PROCESS TO PRODUCE DME

BACKGROUND OF THE INVENTION

The conventional technology for producing dimethyl ether (DME) can be split into two broad categories.

In the first category, DME is produced by dehydrating methanol into DME and byproduct water in a dehydration unit containing a methanol dehydration catalyst where the methanol stream is first produced by converting syngas (i.e. a synthesis gas stream containing hydrogen and carbon monoxide) to methanol in a gas phase reactor containing a methanol synthesis catalyst.

In the second category, the syngas conversion step and methanol dehydration step are combined in a single unit comprising a slurry bubble column reactor (SBCR) containing a bifunctional catalyst system having a methanol synthesis functionality and a methanol dehydration functionality. See for example U.S Pat. No. 5,218,003 assigned to Air Products and Chemicals, Inc.

A concern with the first category is that the gas phase synthesis of methanol produces a relatively high water content crude methanol stream, thereby requiring an intervening water removal unit (i.e. between methanol unit and dehydration unit) and/or an incremental increase in the water that must be processed by the dehydration unit.

One objective of the present invention is to address this concern by selecting a methanol synthesis process that produces a relatively low water content as compared to the gas phase methanol synthesis process. A second objective of the present invention is to provide an alternative to the second category of DME production where it is desired to use a separate methanol synthesis catalyst and a separate methanol dehydration catalyst.

U.S Pat. No. 4,031,123 assigned to Air Products and Chemicals, Inc. (Air Products) teaches a process to produce methanol by converting syngas to methanol in a SBCR containing a methanol synthesis catalyst. Air Products further teaches that while some water is formed in the reaction of the SBCR methanol process, the quantity is small (usually less than 3% of total products). In addition to producing a relatively low water content methanol stream, other advantages of Air Products' SBCR methanol unit as compared to a gas phase methanol unit include the ability to dissipate heat rapidly, the flexibility to process syngas compositions (especially carbon-rich compositions) originating from a wide variety of feedstocks (e.g. coal, natural gas, petroleum coke, waste materials, etc), and even the flexibility to handle fluctuating syngas compositions.

U.S Pat. No. 5,750,799 assigned to Starchem, Inc. (Starchem) teaches a process to produce DME by dehydrating methanol into DME and byproduct water in a dehydration unit containing a methanol dehydration catalyst. Starchem, noting that the methanol feed to the dehydration unit desirably should be relatively free of any water content, teaches methanol feed streams having water contents ranging from about 1 weight % up to about 18 weight %.

Heretofore, the prior art has not captured the advantages of coupling a low water producing SBCR methanol unit to a methanol dehydration unit for DME production.

BRIEF SUMMARY OF THE INVENTION

The present invention is a process for producing DME by dehydrating the effluent stream from a methanol reactor where the methanol reactor is a slurry bubble column reactor (SBCR) containing a methanol synthesis catalyst that converts a synthesis gas stream comprising hydrogen and carbon monoxide into an effluent stream comprising methanol. A key to the process is that the SBCR methanol can produce a relatively low water content methanol stream, thereby avoiding an intervening water removal unit between the SBCR methanol unit and the dehydration unit, and/or an incremental increase in the water that must be processed by the dehydration unit.

DETAILED DESCRIPTION OF THE INVENTION

Figure 1:
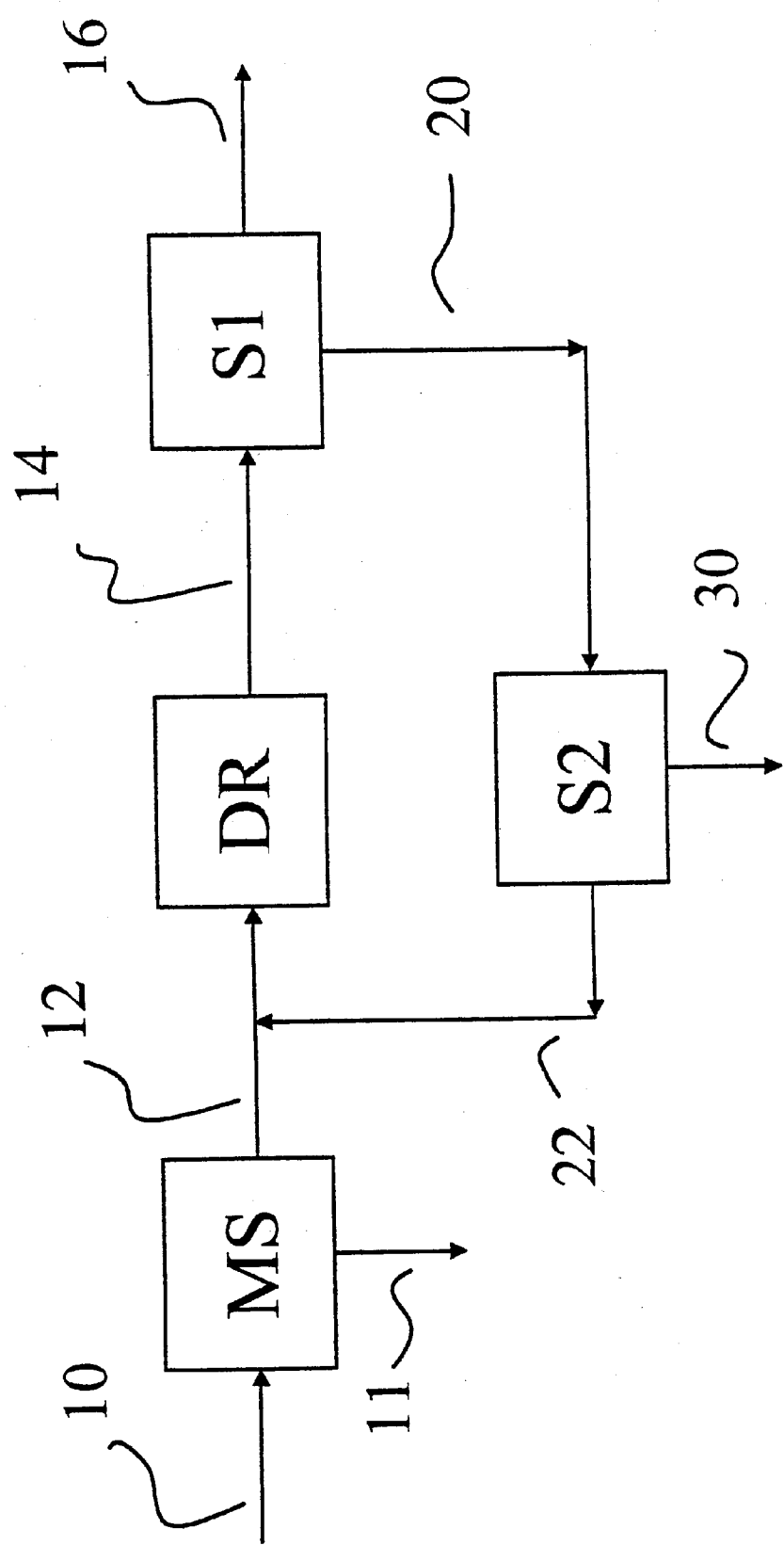
FIG. 1 is a schematic drawing illustrating one embodiment of the present invention.

The process of the present invention is best illustrated with respect to a specific embodiment thereof such as FIG. 1's embodiment.

Referring now to FIG. 1, a synthesis gas stream [10] comprising hydrogen and carbon monoxide is fed to methanol system [MS] comprising a slurry bubble column reactor containing a methanol synthesis catalyst where the synthesis gas stream is converted into an effluent stream [12] comprising methanol, water and higher alcohols (such as ethanol and propanol). The skilled practitioner can appreciate that the synthesis gas stream [10] will also typically contain component gases such as nitrogen, methane and carbon dioxide which typically are purged (along with some unconverted hydrogen and carbon monoxide) from the methanol system as a purge stream [11].

Effluent stream [12] is subsequently fed to a dehydration reactor [DR] containing a methanol dehydration catalyst and converted into an effluent stream [14] comprising the desired DME product. If desired, a portion of methanol effluent stream [12] can be collected as product and not fed to the dehydration reactor.

Dehydration reactor [DR] can be either a fixed bed adiabatic reactor, or a slurry bubble column reactor.

The skilled practitioner can appreciate that effluent stream [14] will also comprise water and unreacted methanol such that, in a preferred embodiment of the present invention, the process further comprises:

(i) separating, in a first separation system [S1] comprising a distillation column, the effluent from the dehydration reactor into a product stream comprising said DME [16] and a byproduct stream [20] comprising said water and unreacted methanol; and (ii) separating, in a second separation system [S2] comprising a distillation column, the byproduct stream [20] into a discharge stream [30] comprising said water and a recycle stream [22] comprising said unreacted methanol which is recycled to the dehydration reactor.

The skilled practitioner can also appreciate that effluent stream [14] from the dehydration reactor will also typically comprise varying amounts of higher alcohols, ethers (such as di-ethyl ether and di-propyl ether) and olefins (such as ethylene and propylene) which eventually become distributed among the DME product stream [16], the water discharge stream [30] and the methanol recycle stream [22].

The skilled practitioner can further appreciate that effluent stream [14] from the dehydration reactor, in addition to comprising higher alcohols, higher ethers and olefins as noted above, will also typically comprise portions of the components in the synthesis gas feed stream that are not completely purged in purge stream [11].

Figure 2:
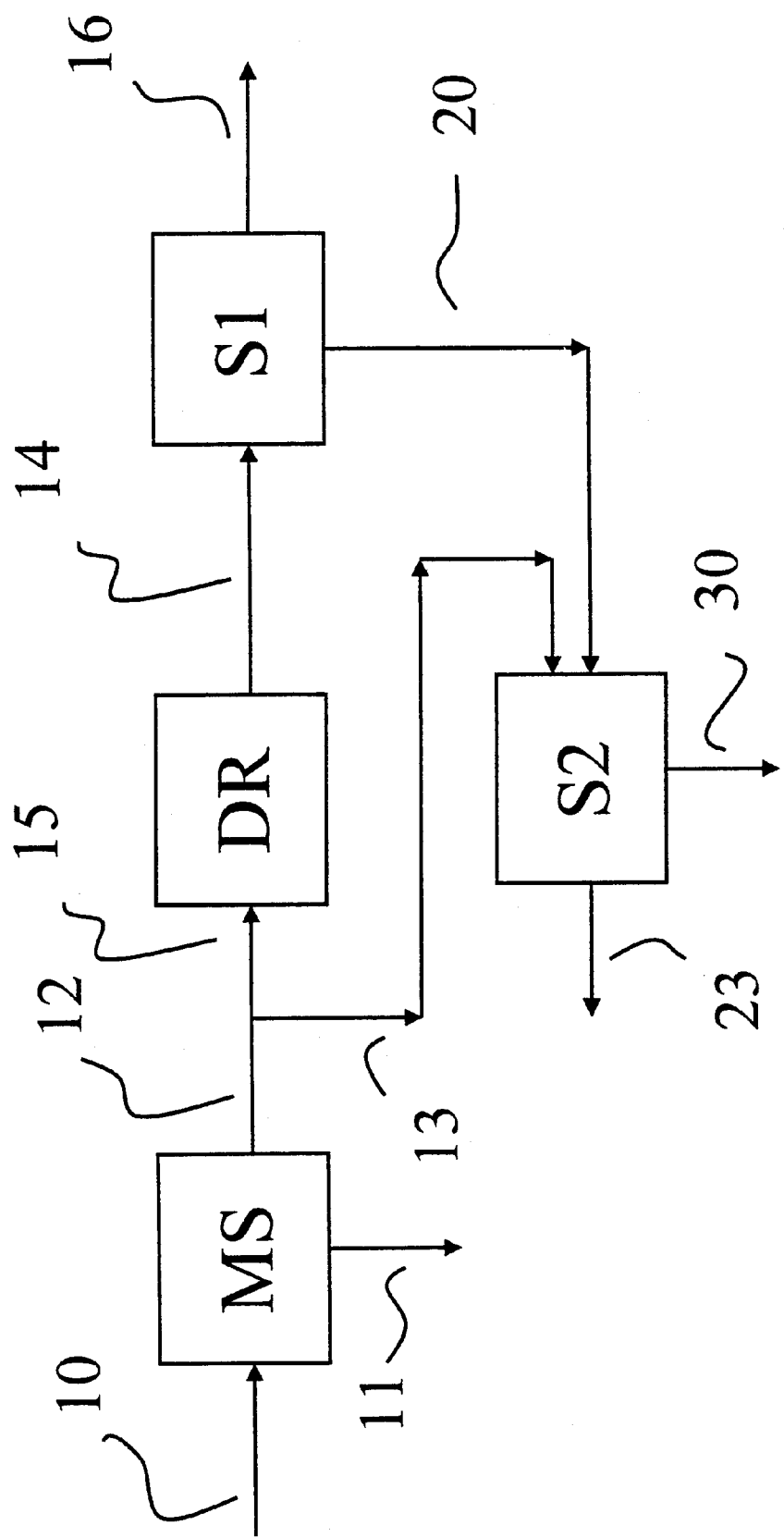
FIG. 2 is a schematic drawing illustrating a second embodiment of the present invention.

FIG. 2 is a second embodiment of the present invention. FIG. 2 is similar to FIG. 1 (common streams and equipment use common identification) except there is a further integration between the methanol system [MS] and the dehydration reactor [DR] designed to produce a co-product stream comprising product grade methanol. In particular, referring to FIG. 2, a portion of the crude methanol effluent from the methanol system is removed as stream [13] and fed directly to the second separation system [S2] (often at a different location in the distillation column), therein by-passing both the dehydration reactor [DR] and the first separation system [S1]. The effluent from the second separation system [S2] is collected as the co-product stream [23] containing product grade methanol.

The skilled practitioner will appreciate that there are many other embodiments of the present invention which are within the scope of the following claims.

What is claimed is:

1. A process for producing DME comprising the steps of:
   (a) converting, in a slurry bubble column reactor (SBCR) containing a catalyst consisting exclusively of a methanol synthesis catalyst, a synthesis gas stream comprising hydrogen and carbon monoxide into an effluent stream comprising methanol and a purge gas stream comprising unconverted hydrogen and carbon monoxide; and
   (b) converting, in a dehydration reactor containing a methanol dehydration catalyst, the effluent stream from step (a) into an effluent stream comprising said DME.

2. The process of claim 1 wherein the effluent stream from step (b) comprising DME also comprises water and unreacted methanol.

3. The process of claim 2 wherein the process further comprises:
   (i) separating the effluent from step (b) into a product stream comprising said DME and a byproduct stream comprising said water and unreacted methanol; and
   (ii) separating the byproduct stream into a discharge stream comprising said water and a recycle stream comprising said unreacted methanol which is recycled to the methanol dehydration reactor.

4. The process of claim 2 wherein the process further comprises:
   (i) removing a portion of the effluent from step (a);
   (ii) separating the effluent from step (b) into a product stream comprising said DME and a byproduct stream comprising said water and unreacted methanol;
   (iii) separating the removed portion of the effluent from step (a) and the byproduct stream into a discharge stream comprising said water and a co-product stream comprising product grade methanol.

5. The process of claim 1 wherein the dehydration reactor is a fixed bed adiabatic reactor.

6. The process of claim 1 wherein the dehydration reactor is a slurry bubble column reactor (SBCR).

* * * * *